US00PP23848P2

(12) United States Plant Patent
Ruter

(10) Patent No.: US PP23,848 P2
(45) Date of Patent: Aug. 27, 2013

(54) BOTTLEBRUSH PLANT NAMED 'RUTCALL'

(50) Latin Name: *Callistemon rigidus*
Varietal Denomination: RutCall

(75) Inventor: John M. Ruter, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 104 days.

(21) Appl. No.: 13/199,100

(22) Filed: Aug. 19, 2011

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — Klarquist Sparkman, LLP

(57) ABSTRACT

A stiff bottlebrush plant having a rounded, non-drooping form, large flowers, long leaves and that begins to flower in late April in Tifton, Ga.

3 Drawing Sheets

Latin name: *Callistemon rigidus*.
Variety denomination: 'RUTCALL'.

ORIGIN OF THE INVENTION

The present invention relates to a new and distinct variety of a stiff bottlebrush plant, *Callistemon rigidus* named 'RutCall'. Seed from an open pollinated stiff bottlebrush plant was planted in a cultivated research area in Tifton, Ga. The new plant was selected while growing in this cultivated area. The plant has been asexually propagated in Tifton, Ga. from semi-hardwood stem cuttings using commercially available rooting hormones.

BRIEF SUMMARY OF THE INVENTION

'RutCall' is a new variety of stiff bottlebrush plant, as evidenced by the following unique combination of characteristics that are outstanding in the new variety and that distinguish it from its parents, as well as from all other varieties of which I am aware:

1. Rounded, non-drooping form.
2. Large flowers.
3. Long leaves.
4. Late flowering.

Asexual reproduction of this new variety by rooting stem cuttings, as performed at Tifton, Ga., shows that the foregoing and all other characteristics and distinctions come true to form and are established and transmitted through succeeding propagations.

COMPARISON WITH *C. RIGIDUS* 'CLEMSON HARDY'

'Clemson Hardy' (unpatented) is a known variety of stiff bottlebrush plant that can be considered an industry standard. For purposes of comparison, a ten year old 'Clemson Hardy' plant growing in Tifton, Ga., was compared with the original 10 year old 'RutCall' plant, also growing in Tifton, Ga. 'RutCall' is a rounded shrub with excellent form in comparison to the sprawling form of 'Clemson Hardy'. The 'RutCall' plant had a height of 3.35 meters and a spread of 4.0 meters in comparison to the 'Clemson Hardy' plant that had a height of 1.8 meters and a spread of 3.0 meters. The inflorescences of the 'RutCall' plant averaged 10 cm to 12 cm in length and 7 cm to 7.5 cm in diameter in comparison to 'Clemson Hardy' flowers which averaged 5.0 cm to 8.0 cm in length and 5.0 cm in diameter. In addition, the leaves of the 'RutCall' plant ranged from 6.0 cm to 9.5 cm in length in comparison to leaves that were 6.0 cm in length for the 'Clemson Hardy' plant. In addition, the 'RutCall' plant began to flower in late April in Tifton, Ga. in comparison to 'Clemson Hardy' which began flowering in mid to late March.

COMPARISON TO SEED PARENT

The new plant is a generally rounded, non-drooping shrub. In contrast, the seed parent is a sprawling non-uniform plant.

BRIEF DESCRIPTION OF THE ILLUSTRATIONS

The accompanying illustrations show the 'RutCall' plant in color as nearly true as it is reasonably possible to make the same in a color illustration of this character.

DETAILED BOTANICAL DESCRIPTION

Figure 1:
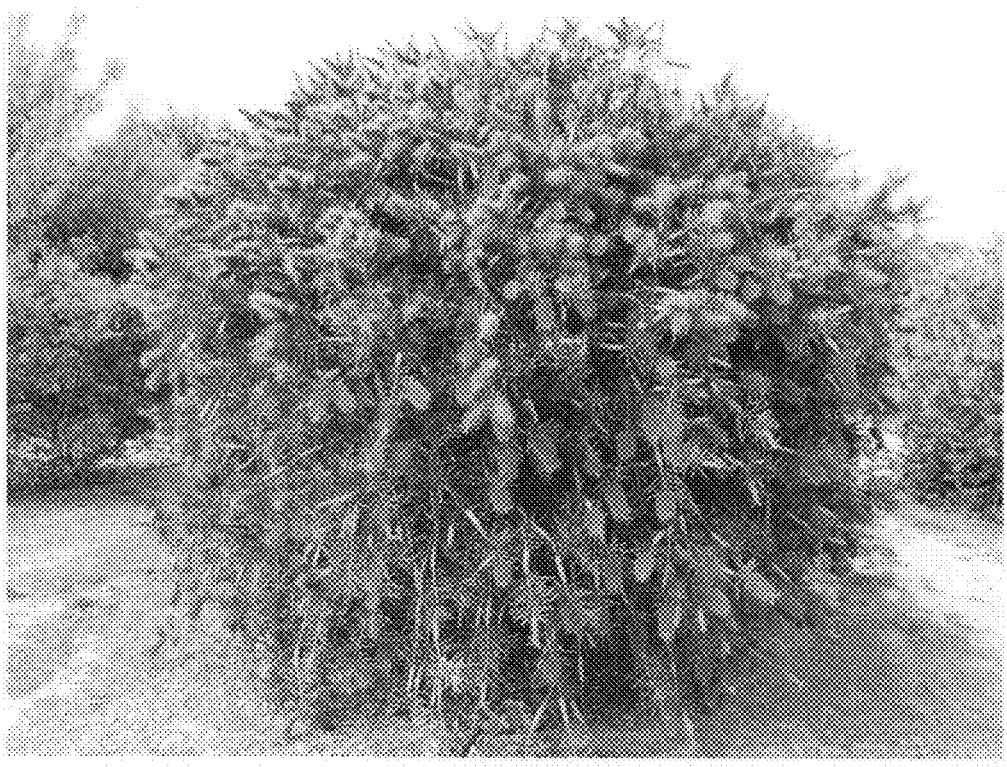
FIG. 1 is a photograph of the ten year old 'RutCall' stiff bottlebrush plant.
Figure 2:
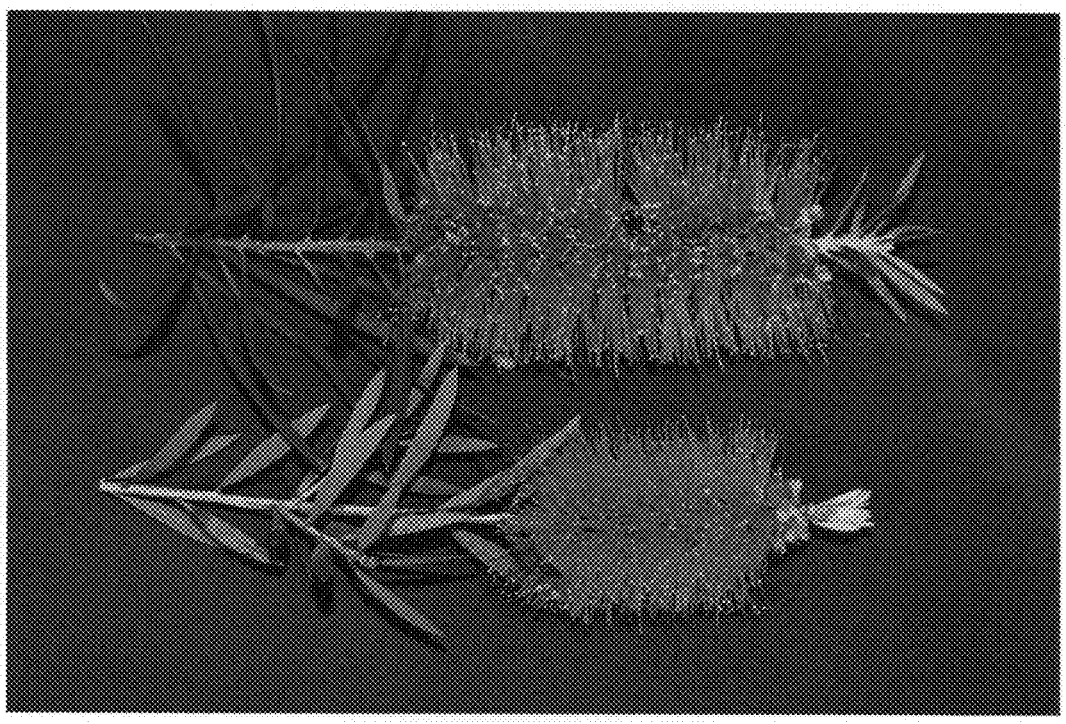
FIG. 2 illustrates a flower and leaves of the 'RutCall' stiff bottlebrush plant in the upper portion of the photograph, and a flower and leaves of the 'Clemson Hardy' stiff bottlebrush plant in a lower portion of the photograph.
Figure 3:
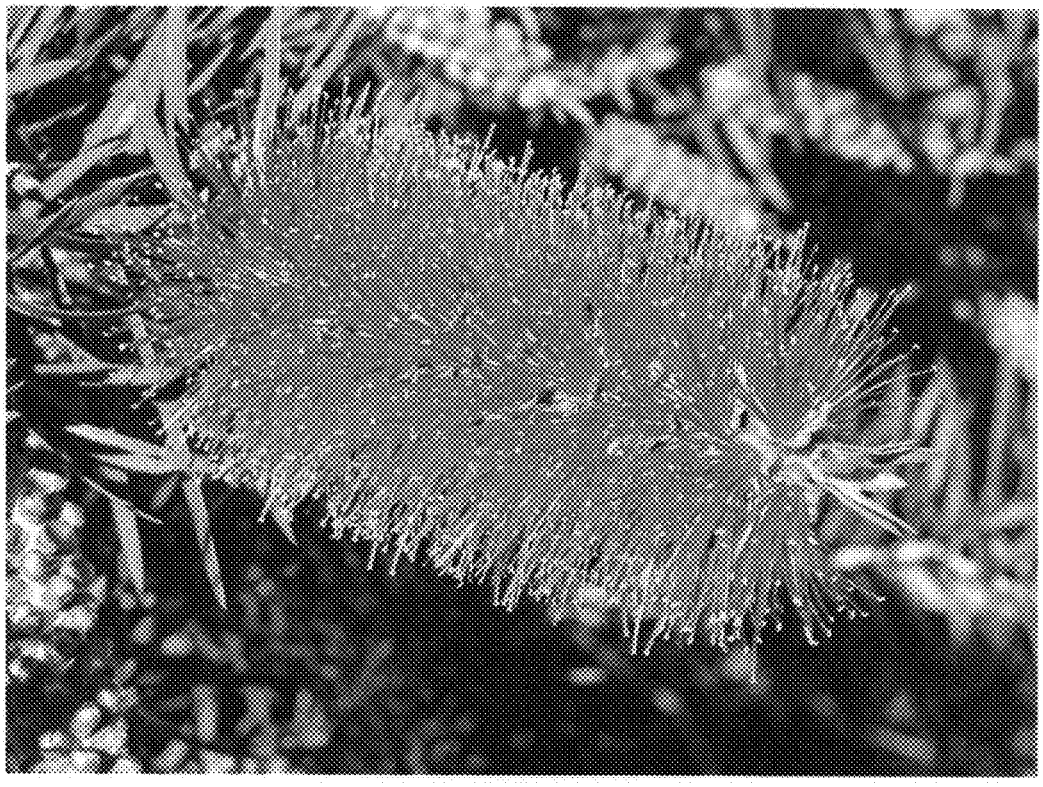
FIG. 3 is a photograph of another flower of the 'RutCall' stiff bottlebrush plant.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart, 2001. The colors of an illustration of this type may vary with lighting and other conditions. Therefore, color characteristics of this new variety should be determined with reference to the observations described herein, rather than from these illustrations alone.

Observations are of the ten year old original 'RutCall' plant growing in Tifton, Ga., and of five year old asexually propagated progeny thereof.

Parentage:

*Seed parent.*—Unnamed *Callistemon rigidus* stiff bottlebrush plant.

*Pollen parent.*—Unknown *Callistemon rigidus* stiff bottlebrush plant.

FLOWER

Blooming habit: Blooming (first color) in late April in Tifton, Ga.

Inflorescence: One spike per inflorescence, inflorescence comprised of many florets with exserted stamens that obscure the flowers.

*Spike-shape.*—Generally cylindrical, color presented by exserted stamens and stigma: Red (RHS 53 B); Attachment: sessile; Project generally perpendicular to stem.

*Overall size.*—Length typically 10.0 cm to 12.0 cm. Average diameter is about 7.0 cm to 7.5 cm.

*Form.*—Bottlebrush shape, dense generally of a cylindrical overall shape.

*Individual flowers.*—Minute; corolla comprised of petals that open to be five in number, ovate, unfused, self-cleaning, not-fragrant, color of both petal surfaces approximates Green (RHS 143A); Calyx — inconspicuous; Sepals — make up the calyx.

*Buds.*—Obtuse shape, about 2 mm in length, about 1.5 mm in diameter; color is Greyed-Orange (RHS 175 C).

Reproductive parts:

*Stamens.*—Number: Typically 36 stamens per floret. Color: Red (RHS 53 B). Length: Typically 2.5 cm. Arrangement: Free. Anthers: Dimensions: Minute — about 1 mm in length. Color: Red (RHS 53A). Pollen: Color: Yellow-Green (RHS 153 B), moderate amount of pollen present.

*Pistil.*—Number: one per flower. Style: Color: Red (RHS 53 B). Length: Typically 3.0 cm. Stigmas: Color: Yellow-Green (RHS 144A).

Seeds and fruit: Fruit color: Greyed-Orange (RHS 165 C); Seeds minute, color: Grey (RHS 201D); Dehiscent flowers leave persistent sessile seed capsules grouped tightly along stem; Capsules — spherical, approximately 7 mm in diameter.

PLANT

*Form.*—Rounded, non-drooping shrub.

*Ten year old plant.*—Height: 3.35 meters. Width: 4.0 meters.

Foliage:

*Type.*—Evergreen.

*Leaf shape.*—Linear to oblanceolate, base and apex are acute.

*Division.*—Simple.

*Size of mature leaf.*—About 6.0 cm to 9.5 cm long; 0.5 cm wide.

*Color.*—Upper surface (adaxial): Yellow-Green (RHS 139 A). Lower Surface (abaxial): Yellow-Green (RHS 147 A).

*Texture.*—Leathery; glabrous when mature.

*Margins.*—Entire.

*Arrangement.*—Whorled.

*Petiole.*—Length: Typically 0.3 cm. Color: Yellow-Orange (RHS 21 C).

*Vein color.*—Upper surface: (RHS 139A). Lower surface: (RHS 147A).

*Venation pattern.*—Parallel.

Stem:

*Shapes.*—Cylindrical.

*Color.*—Mature stems: Greyed-Green (RHS 197 C) New growth stems: Grey-Orange (RHS 175A).

*Dimensions.*—Typical stem length 5-10 cm. Typical stem diameter: 2-3 mm.

*Internode length.*—0.5 cm to 0.7 cm.

*Texture.*—Ridged with age (third year growth).

Winter hardiness: Has been grown in Georgia locations (USDA 8a) where temperatures do not regularly drop below 15° F.

Disease and pest resistance: No unique disease or pest resistance has been observed to date.

I claim:

1. A new and distinct variety of stiff bottlebrush plant, substantially as herein shown and described.

* * * * *